(12) United States Patent
Doerr et al.

(10) Patent No.: US 11,071,871 B2
(45) Date of Patent: Jul. 27, 2021

(54) SYSTEM WITH AN INTRACARDIAC PACEMAKER AND A COVER FOR THE PACEMAKER

(71) Applicant: BIOTRONIK SE & CO. KG, Berlin (DE)

(72) Inventors: Thomas Doerr, Berlin (DE); Dirk Muessig, West Linn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 120 days.

(21) Appl. No.: 16/203,671

(22) Filed: Nov. 29, 2018

(65) Prior Publication Data

US 2019/0192866 A1  Jun. 27, 2019

(30) Foreign Application Priority Data

Dec. 22, 2017  (EP) ..................... 17210083

(51) Int. Cl.
| | |
|---|---|
| *A61N 1/375* | (2006.01) |
| *A61L 31/14* | (2006.01) |
| *A61N 1/372* | (2006.01) |
| *A61L 31/18* | (2006.01) |
| *A61L 31/16* | (2006.01) |
| *A61B 46/13* | (2016.01) |
| *A61N 1/05* | (2006.01) |
| *A61B 5/00* | (2006.01) |
| *A61N 1/39* | (2006.01) |

(52) U.S. Cl.
CPC .......... *A61N 1/37512* (2017.08); *A61B 46/13* (2016.02); *A61L 31/14* (2013.01); *A61L 31/148* (2013.01); *A61L 31/16* (2013.01); *A61L 31/18* (2013.01); *A61N 1/05* (2013.01); *A61N 1/375* (2013.01); *A61N 1/3756* (2013.01); *A61N 1/37205* (2013.01); *A61B 5/686* (2013.01); *A61L 2300/222* (2013.01); *A61L 2300/41* (2013.01); *A61L 2400/12* (2013.01); *A61N 1/3956* (2013.01)

(58) Field of Classification Search
CPC combination set(s) only.
See application file for complete search history.

(56) References Cited

U.S. PATENT DOCUMENTS

| | | | |
|---|---|---|---|
| 5,090,422 A | 2/1992 | Dahl et al. | |
| 9,023,114 B2* | 5/2015 | Buevich | A61N 1/375 623/23.75 |
| 2010/0168808 A1* | 7/2010 | Citron | A61L 31/146 607/5 |
| 2011/0046713 A1* | 2/2011 | Cully | A61F 2/95 623/1.13 |

(Continued)

FOREIGN PATENT DOCUMENTS

| | | |
|---|---|---|
| WO | 2005039691 A1 | 5/2005 |
| WO | 2014137454 A1 | 9/2014 |

*Primary Examiner* — Gary Jackson
*Assistant Examiner* — Zahed Kabir
(74) *Attorney, Agent, or Firm* — Laurence A. Greenberg; Werner H. Stemer; Ralph E. Locher

(57) ABSTRACT

An intracardiac system has an intracardiac pacemaker and a cover. The cover at least partially surrounds the pacemaker. An inner surface of the cover, which faces the pacemaker, includes an inner layer with bioresorbable material. There are also described methods for implanting and explanting an intracardiac pacemaker.

14 Claims, 3 Drawing Sheets

(56) References Cited

U.S. PATENT DOCUMENTS

| | | | |
|---|---|---|---|
| 2013/0218125 A1* | 8/2013 | Stopek | A61M 5/00 604/500 |
| 2015/0086604 A1* | 3/2015 | Buevich | A61L 31/048 424/426 |

* cited by examiner

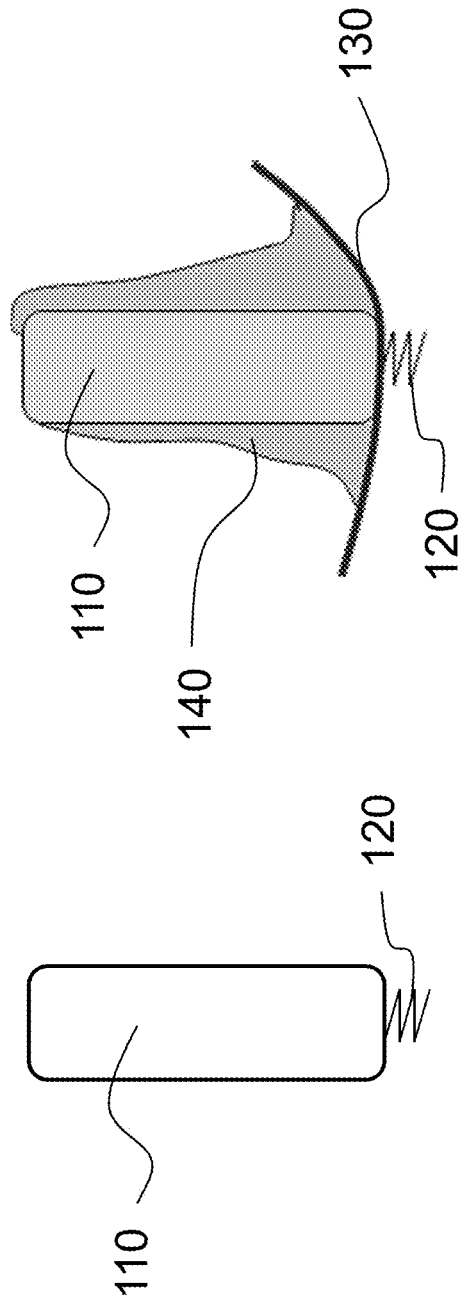

SYSTEM WITH AN INTRACARDIAC PACEMAKER AND A COVER FOR THE PACEMAKER

CROSS-REFERENCE TO RELATED APPLICATION

This application claims the priority, under 35 U.S.C. § 119, of European patent application EP 17210083.6, filed Dec. 22, 2017; the prior application is herewith incorporated by reference in its entirety.

BACKGROUND OF THE INVENTION

Field of the Invention

The invention relates to a system with an intracardiac pacemaker and a cover for the pacemaker.

Implantable devices are used in order to address several aspects of health. The implantable devices include active implants, such as pacemakers or implantable cardioverter-defibrillators, and drug delivery devices.

In particular in the case of an intracardiac pacemaker, removal (i.e., explantation) is a complex task. The intracardiac pacemaker is overgrown with tissue a few weeks after its implantation, which makes a removal of the intracardiac pacemaker very difficult.

European patent No. EP 0 773 753 B1 discloses an implantable apparatus including a drug delivery device which is surrounded by a porous polymeric material.

U.S. Pat. No. 5,090,422 discloses an electrically active implant, such as an implantable cardioverter-defibrillator, which is covered by a porous barrier.

SUMMARY OF THE INVENTION

It is an object to provide improved technologies for intracardiac implants. In particular, explantation of an intracardiac implant shall be simplified.

With the above and other objects in view there is provided, in accordance with the invention a system, comprising:
an intracardiac pacemaker;
a cover at least partially surrounding said pacemaker, said cover having an inner surface facing said pacemaker, said inner surface including an inner layer of a bioresorbable material.

In accordance with the invention, there is provided a system comprising an intracardiac implant, e.g. an intracardiac pacemaker, and a cover. The cover at least partially surrounds the implant.

In accordance with a further feature of the invention, there is described a method for implanting an intracardiac implant, e.g. an intracardiac pacemaker. The method comprises steps of: providing an intracardiac implant, providing a cover, arranging the implant in the cover such that the cover at least partially surrounds the implant, and arranging the implant with the cover inside a heart of a patient, e.g. in the atrium or in the ventricle of the heart.

In accordance with yet another feature of the invention, there is described a method for explanting an intracardiac implant, e.g. an intracardiac pacemaker, at least partially surrounded by a cover. The method comprises steps of: opening the cover, and removing the intracardiac implant from the cover.

In the application, the term "implant" refers to an "intracardiac implant," an implantable device which is arranged inside the heart of a patient, e.g. in the atrium or in the ventricle. The implant may be an intracardiac pacemaker (also referred to as a leadless pacemaker).

The cover may be made of a biocompatible and/or biostable material.

In an implanted state, when the implant with the cover is arranged inside the heart, a proximal end of the cover (and a proximal end of the implant) is adjacent to the inner surface of the heart. A distal end of the cover (and a distal end of the implant) is facing away from the inner surface of the heart. The cover may have an opening at the proximal end of the cover. A fixation element may be disposed at the proximal end of the implant. The fixation element may reach through the opening of the cover and be in contact with tissue of the heart in order to fix the implant with the cover in the myocardium.

The implant may be arranged in the cover such that the cover surrounds the implant on all sides except its proximal end (the side facing the inner surface of the heart). After the implant with the cover is implanted in the heart, tissue will grow over the cover. After some time, the cover will be partly or completely overgrown with tissue.

For explantation, i.e., for the removal of the intracardiac device, the cover may be opened, e.g. at its distal end, in order to retrieve the implant from the cover. The cover itself may remain in the patient after the implant is explanted. The cover may be opened by cutting the cover. The cover may be cut by a nose which is guided by a catheter. A marker element, e.g. an X-ray marker, may be disposed at the distal end of the cover in order to provide guiding for cutting the cover.

An inner surface of the cover, which is facing the implant, may comprise an inner layer comprising a bioresorbable material. The inner layer may be made of a bioresorbable material. The bioresorbable material may be a bioresorbable polymer, e.g. RESOMER® provided by Evonik. After the implant is removed from the cover, the bioresorbable material is resorbed. This leads to a reduced volume of the cover remaining in the heart.

An outer surface of the cover, which is facing away from the implant, may comprise an outer layer comprising a non-bioresorbable material. The outer layer may be made of a non-bioresorbable material. The non-bioresorbable material may be a poly(p-xylylene) polymer, e.g. a Parylene (e.g., Parylene C, Parylene N, or Parylene AF-4). The outer layer may be thin. The non-bioresorbable material may have a thickness in the range from 0.1 µm (e.g. Parylene) to 1 mm (e.g. Silicone).

In accordance with a further feature of the invention, the cover is made of a flexible material, e.g. silicone or expanded polytetrafluoroethylene (ePTFE). After the implant is removed from the cover, the cover may collapse. The collapsed cover requires less volume.

In accordance with another feature of the invention, the cover is made of a non-porous material. Hereby, a contact of the implant with body fluid (e.g. blood) can be avoided. In an alternative embodiment, the cover may be made of a porous material.

The cover may comprise one or more predetermined breaking points. The predetermined breaking point(s) may allow an easy opening of the cover for explanting the implant. The predetermined breaking point(s) may be disposed at the distal end of the cover. The predetermined breaking point(s) may be provided in form of a pressure lock, a seal bag or by a tapering of the cover at its distal end. A distal opening provided by the predetermined breaking point(s) may be used for inserting a new implant in the cover after the (original) implant is removed.

The cover may comprise a marker element, e.g. one or more X-ray markers, for identifying the predetermined breaking point(s). The marker element may be a fluid X-ray contrast agent. The X-ray contrast agent may be resorbed or discarded after the cover is opened.

The cover may comprise opening means which allow opening the cover. The opening means may be a filament or a wire which may be embedded in the cover. By pulling the filament or the wire, the cover is opened.

The outer surface of the cover may have a roughened surface structure. The roughened surface structure may support ingrowth of the cover in tissue of the heart which may lead to an improved fixation of the implant.

The outer surface of the cover, or at least a part of the outer surface, preferably in a distal region, may comprise nanotubes or an anti-inflammatory coating, e.g. a steroid. Hereby, ingrowth of the cover in tissue may be inhibited.

The cover may be permeable or selectively permeable. For example, the cover may be permeable for body fluid such that body fluid may contact the implant and may transfer electrical charge. The implant may be used as a biochemical sensor, e.g. for K+, Na+, Ca+ or other electrolytes, biochemical markers like NT-proBNP, Kidney markers like Cystatine C, Glucose and others.

The inner surface of the cover may have a hydrophilic coating and/or a coating with a low coefficient of friction. This may reduce resistance when removing the implant from the cover.

The cover may comprise an electrically conductive material. Hereby, the cover may be used as an electrode.

The cover may comprise an electrically insulating material. In that case, the cover acts as an insulator.

It will be understood that the features disclosed in regard with the system may also apply to the methods and vice versa.

Other features which are considered as characteristic for the invention are set forth in the appended claims.

Although the invention is illustrated and described herein as embodied in a system with an intracardiac pacemaker and a cover for the pacemaker, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1A is an elevation view of an implantable intracardiac pacemaker (leadless pacemaker);

FIG. 1B shows the pacemaker implanted and partially overgrown by heart tissue;

Same reference numerals are used for identical or functionally identical components throughout the figures.

DETAILED DESCRIPTION OF THE INVENTION

Figure 2B:
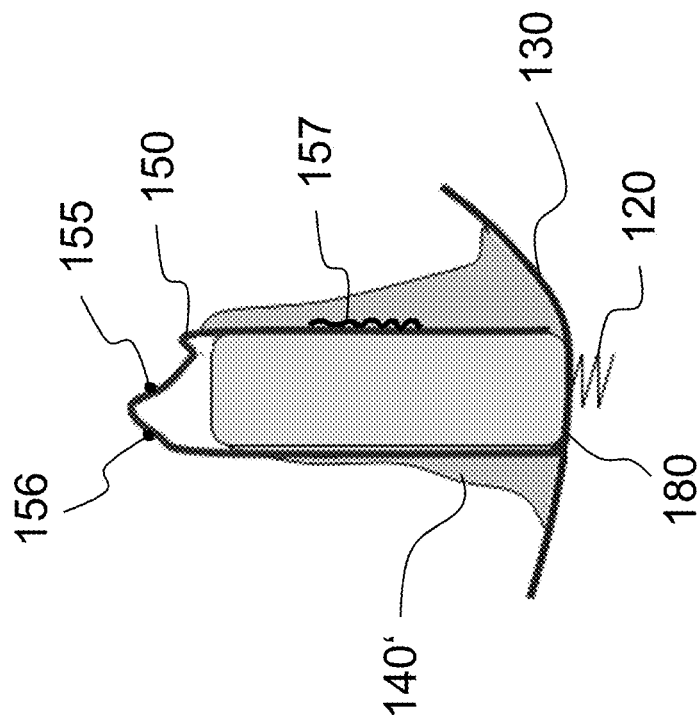
FIG. 2B shows the implanted pacemaker with the cover.

Referring Now to the Figures of the Drawing in Detail, FIG. 1A shows an implantable intracardiac pacemaker 110 with a fixation element 120. The fixation element 120 is disposed at a proximal end of the intracardiac pacemaker 110. The fixation element 120 may be a screw or may be formed by one or more tines (not shown). The intracardiac pacemaker 110 includes an energy source (e.g. a battery) and a control unit (e.g., a processor) which is configured for generating pacing pulses for the heart. The energy source and the control unit may be enclosed by an implant body. The implant body may be encapsulated.

Using conventional procedures, the implantable intracardiac pacemaker 110 is implanted in the heart of a patient, for instance in the atrium or in the ventricle. The implantable intracardiac pacemaker is fixed to the myocardium 130 by the fixation element 120. Several weeks after the implantation, the intracardiac pacemaker is overgrown by tissue 140 as shown in FIG. 1B. Since a large portion of the surface (or even the complete surface) of the intracardiac pacemaker 110 is covered by the tissue 140, it is not possible to explant the intracardiac pacemaker 110 in an easy and safe manner.

Figure 2A:
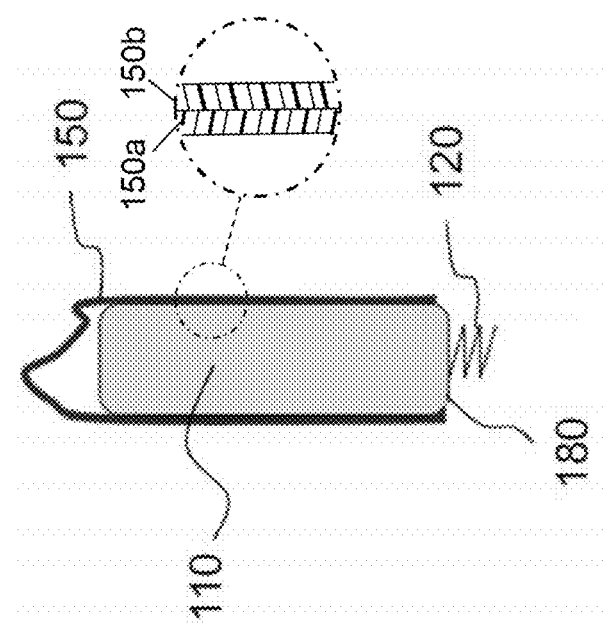
FIG. 2A is an elevation view of an implantable intracardiac pacemaker with a cover.

FIG. 2A shows an implantable intracardiac pacemaker 110 which is surrounded at least in part by a cover 150. The cover 150 may also be called an explantation cover. The cover 150 has an opening 180 which is formed at a proximal end of the cover 150. After the intracardiac pacemaker 110 with the cover 150 is implanted in a heart, tissue 140' grows and covers the cover 150 (cf. FIG. 2B). The cover may be made of a biocompatible and/or biostable material, e.g. silicone or polyurethane (PU).

The outer surface of the cover 150 may be formed with nanotubes or an anti-inflammatory coating at least in parts thereof. The nanotubes or anti-inflammatory coating are illustrated highly diagrammatically and indentified with reference numeral 157.

The cover may be formed with one or more predetermined breaking points 155. The breaking point(s) allows an easy opening of the cover for explanting the implant. The predetermined breaking point(s), as diagrammatically indicated, is preferably disposed at the distal end of the cover. The predetermined breaking point(s) may be a pressure lock, a seal bag or simply a tapering of the cover at its distal end. A distal opening provided by the predetermined breaking point(s) may be used for inserting a new implant in the cover after the (original) implant is removed. There may also be provided a marker element, e.g. one or more X-ray markers, for identifying the predetermined breaking point(s) 155. The marker element may be a fluid X-ray contrast agent. The X-ray contrast agent may be resorbed or discarded after the cover is opened. There may also be provided an opening aid 156 by way of which the cover is opened. It may be a filament or a wire, similar to a pull string, which may be embedded in the cover 150. By pulling the filament or the wire, the cover is opened.

Figure 3B:
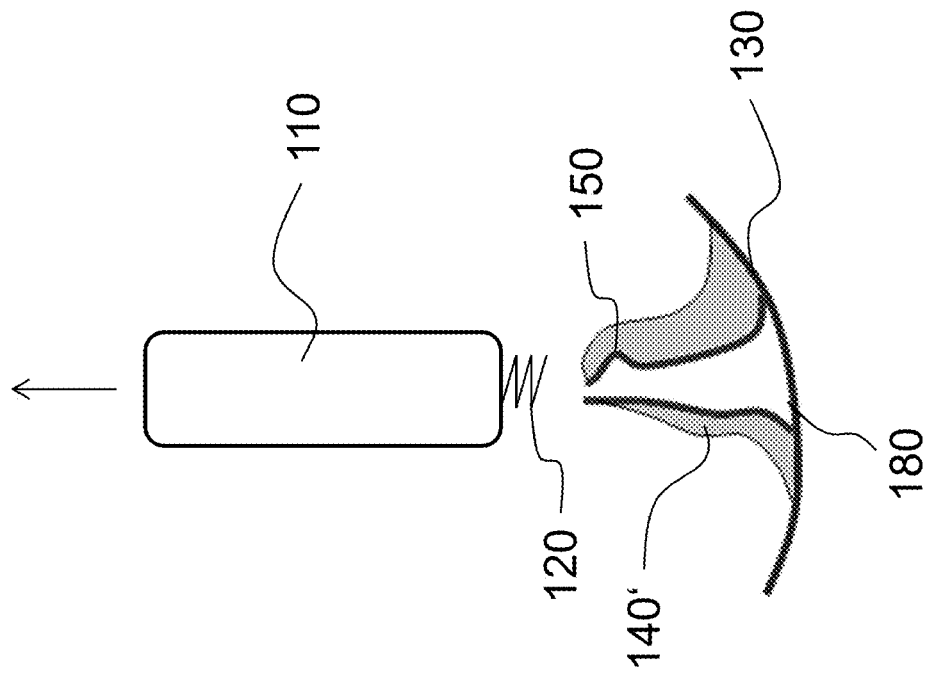
FIGS. 3A and 3B show two steps in the explantation of the intracardiac pacemaker.
Figure 3A:
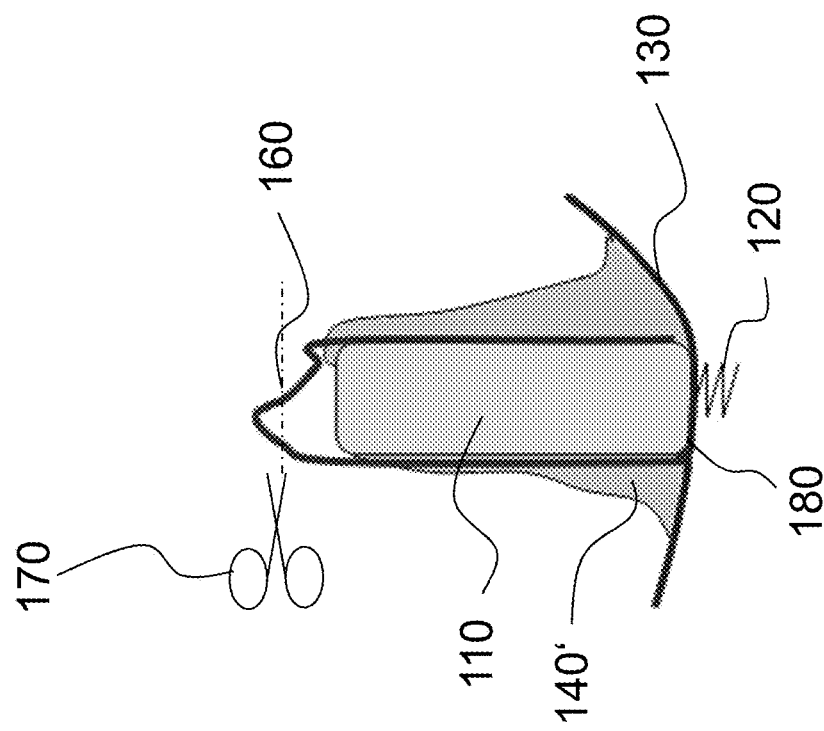

FIGS. 3A and 3B show a schematic view of an explantation of the intracardiac pacemaker 110 with the cover 150. For example, the intracardiac pacemaker 110 may be removed from the heart when the battery is empty. In a first step, the cover 150 is opened at a distal end 160. The cover 150 may be opened by a catheter-based tool 170 (cf. FIG.

3A). Alternatively, the cover may be opened by an opening means that is integrated in the cover (not shown).

After the cover 150 is opened, the intracardiac pacemaker 110 is removed (FIG. 3B). The empty cover 150 collapses and remains in the heart. In case the inner surface 150a (cf. FIG. 2A) of the cover 150 comprises a bioresorbable material, the bioresorbable material of the inner surface 150a starts to be resorbed, leaving only the outer surface 150b of the cover 150 and further reducing the volume of the remaining cover.

The opening means 156 itself or a part of it, e.g. a wire, may be made of an X-ray dense material to be visible during an X-ray guided explant procedure.

The features disclosed in the specification, the claims and the figures may be relevant for realizing embodiments either alone or in any combination with each other.

The following is a summary list of reference numerals and the corresponding structure used in the above description of the invention:

110 intracardiac pacemaker
120 fixation element
130 myocardium
140 tissue on intracardiac pacemaker
140' tissue on cover
150 cover
155 breaking point, x-ray marker
156 pull string (filament, wire)
157 nanotubes, anti-inflammatory coating
160 distal end of the cover
170 tool
180 opening

The invention claimed is:

1. A system, comprising:
an intracardiac pacemaker;
a cover at least partially surrounding said pacemaker, said cover having an inner surface facing said pacemaker, said inner surface including an inner layer of a bioresorbable material; and
said cover having an outer surface facing away from said pacemaker, said outer surface including an outer layer of a non-bioresorbable material.

2. The system according to claim 1, wherein said cover is made of a flexible material.

3. The system according to claim 1, wherein said cover is formed with a predetermined breaking point.

4. The system according to claim 3, wherein said cover comprises a marker element for identifying said predetermined breaking point.

5. The system according to claim 1, wherein said cover comprises opening means which allow opening said cover.

6. The system according to claim 1, wherein said outer surface of said cover has a roughened surface structure.

7. The system according to claim 1, wherein said outer surface of said cover comprises nanotubes or an anti-inflammatory coating at least in parts of said outer surface.

8. The system according to claim 1, wherein said cover is permeable or selectively permeable.

9. The system according to claim 1, wherein said inner surface of said cover has a hydrophilic coating and/or a coating with a low coefficient of friction.

10. The system according to claim 1, wherein said cover comprises an electrically conductive material.

11. The system according to claim 1, wherein said cover comprises an electrically insulating material.

12. A method for implanting an intracardiac pacemaker, the method comprising:
providing an intracardiac pacemaker;
providing a cover with an inner surface configured to form the pacemaker when the pacemaker is inserted in the cover, the inner surface having an inner layer of a bioresorbable material and an outer layer of a non-bioresorbable material;
arranging the pacemaker in the cover such that the cover at least partially surrounds the pacemaker; and
implanting the pacemaker with the cover inside a heart of a patient.

13. A method for explanting an intracardiac pacemaker, wherein the pacemaker is at least partially surrounded by a cover, wherein an outer surface of the cover is formed of a non-bioresorbable material and an inner surface of the cover that faces the pacemaker includes an inner layer of a bioresorbable material, the method comprising:
opening the cover; and
removing the intracardiac pacemaker from the cover; and
allowing the bioresorbable material to become subsequently resorbed and to reduce a volume of the cover.

14. A system, comprising:
an intracardiac pacemaker;
a cover at least partially surrounding said pacemaker, said cover having an inner surface facing said pacemaker and an outer surface facing away from said pacemaker;
said cover being made of a non-porous material, said inner surface including an inner layer of a bioresorbable material, and said outer surface including an outer layer of a non-bioresorbable material.

* * * * *